United States Patent
Abele et al.

(10) Patent No.: US 6,271,406 B1
(45) Date of Patent: Aug. 7, 2001

(54) PROCESS FOR THE PREPARATION OF HALOGENATED 1,2-DISILAETHANES

(75) Inventors: Bors C. Abele; Jörn Winterfeld, both of Burghausen (DE)

(73) Assignee: Wacker-Chemie GmbH, München (DE)

(*) Notice: Subject to any disclaimer, the term of this patent is extended or adjusted under 35 U.S.C. 154(b) by 0 days.

(21) Appl. No.: 09/715,581

(22) Filed: Nov. 17, 2000

(30) Foreign Application Priority Data

Nov. 25, 1999 (DE) .............................. 199 56 810

(51) Int. Cl.$^7$ ..................................................... C07F 7/08
(52) U.S. Cl. ............................................. 556/431; 556/435
(58) Field of Search ..................... 556/431, 435

(56) References Cited

U.S. PATENT DOCUMENTS

| | | |
|---|---|---|
| 3,041,362 | 6/1962 | Merker . |
| 3,220,972 | 11/1965 | Lamoreaux . |
| 3,497,539 | 2/1970 | Goossens . |
| 3,674,739 | 7/1972 | Goossens . |
| 3,798,252 | 3/1974 | Nitzsche et al. . |
| 5,527,934 * | 6/1996 | Jung et al. ........................... 556/435 |
| 5,596,117 * | 1/1997 | Itoh et al. ........................... 556/431 |

FOREIGN PATENT DOCUMENTS

| | | |
|---|---|---|
| 2 001 303 | 7/1971 | (DE) . |
| 2 131 741 | 12/1972 | (DE) . |
| 2 131 742 | 12/1972 | (DE) . |

OTHER PUBLICATIONS

Kumada et al., J. Organometal Chem. 1967, 10(1), pp. 111–119.

Ishikawa et al., J. Organometal Chem. 1970, 23(1), pp. 63–69.

H. Sakurai et al., Tetrahedron Letters 1966, 45, pp. 5493–5497.

Suryanarayanan et al., J. Organometal Chem. 1973, 55(1), pp. 65–71.

English Derwent Abstract Corresponding To DE 2 001 303, Jul. 1971.

English Derwent Abstract Corresponding To DE 2 131 742, Dec. 1972.

* cited by examiner

Primary Examiner—Paul F. Shaver
(74) Attorney, Agent, or Firm—Brooks & Kushman P.C.

(57) ABSTRACT

A process for the preparation of halogenated 1,2-disilaethanes of the general formula $$X_{3-n}R_nSi\text{—}CHR^1CHR^1\text{—}SiR_nX_{3-n} \qquad (I)$$

in which R may be identical or different and denotes a hydrogen atom or a monovalent optionally substituted hydrocarbon radical having 1 to 40 carbon atom(s) per radical, $R^1$ may be identical or different and denotes a hydrogen atom or a monovalent optionally substituted hydrocarbon radical having 1 to 40 carbon atom(s) per radical, X denotes a halogen atom and n denotes 0, 1 or 2, wherein halogenated 1,2-disilaethenes of the general formula $$X_{3-n}R_nSi\text{—}CR^1\text{=}CR^1\text{—}SiR_nX_{3-n} \qquad (II)$$

in which R, $R^1$, X and n have the meaning stated above therefor, are reacted with hydrogen in the presence of promoting catalysts. The product is produced in high yield and purity.

15 Claims, No Drawings

PROCESS FOR THE PREPARATION OF HALOGENATED 1,2-DISILAETHANES

TECHNICAL FIELD

The invention relates to a process for the preparation of halogenated 1,2-disilaethanes.

BACKGROUND ART

A large number of processes for the preparation of halogenated 1,2-disilaethanes are known. Thus, they are obtainable via hydrosilylation reactions. For example, the preparation of 1,2-bis(chlorodimethylsilyl)ethane is carried out via the hydrosilylation reaction between chlorodimethylsilane and chlorodimethylvinylsilane. The hydrosilylation reactions are described in U.S. Pat. Nos. 3,041,362, 3,497,539, 3,220,972, 3,674,739, DE-A 2 131 74 1 and the corresponding U.S. Pat. No. 3,798,252 (Wacker-Chemie GmbH, published on Mar. 19, 1974) and DE-A 2 131 742 (Wacker-Chemie GmbH, laid open on Dec. 28, 1972).

Further processes for the preparation of 1,2- bis(chlorodimethylsilyl)-ethane are chlorination reactions of bis(trimethylsilyl)ethane (Kumada et al., J. ORGANOMET. CHEM. 1967, 10(1), 111–119, and Ishikawa et al., J. ORGANOMET. CHEM. 1970, 23(1), 63–69). It is also known that halogenated 1,2-disilaethanes can be prepared by reacting disilanes with organyl chlorides or HCl (H. Sakurai et al., TETRAHEDRON LETT. 1966, 45, 5493–7). 1, 2-Bis(chlorodimethylsilyl)ethane is also obtainable via the hydrosilylation of dimethylmethoxyvinylsilane with chlorodimethylsilane (Suryanarayanan et al., J. ORGANOMET. CHEM. 1973, 55(1), 65–71).

DE-A 2 131 741 and the corresponding U.S. Pat. No. 3,798,252 (Wacker-Chemie GmbH, published on Mar. 19, 1974), DE-A2 131 742 (Wacker-Chemie GmbH, laid open on Dec. 28, 1972) and DE-A 2 001 303 (Wacker-Chemie GmbH, laid open on Jul. 22, 1971) describe halogenated 1,2-disilaethanes, such as 1,2-bis(chlorodimethylsilyl)ethane, as solvents in the preparation of alkenylsilanes, such as chlorodimethylvinylsilane.

DISCLOSURE OF THE INVENTION

It was an object of the present invention to provide a process for the preparation of halogenated 1,2-disilaethanes which is simple, the halogenated 1,2-disilaethanes being obtained in high yield and purity over a short reaction time. It was a further object to provide a particularly economical and environmentally friendly process for the preparation of halogenated 1,2-disilaethanes. These and other objects are achieved by the present invention.

DETAILED DESCRIPTION OF THE INVENTION

The invention relates to a process for the preparation of halogenated 1,2-disilaethanes of the general formula $$X_{3-n}R_nSi-CHR^1CHR^1-SiR_nX_{3-n} \qquad (I),$$

in which R may be identical or different and denotes a hydrogen atom or a monovalent optionally substituted hydrocarbon radical having 1 to 40 carbon atom(s) per radical, $R^1$ may be identical or different and denotes a hydrogen atom or a monovalent optionally substituted hydrocarbon radical having 1 to 40 carbon atom(s) per radical, X denotes a halogen atom, and n denotes 0, 1 or 2, wherein halogenated 1,2-disilaethenes of the general formula $$X_{3-n}R_nSi-CR^1=CR^1-SiR_nX_{3-n} \qquad (II),$$

in which R, $R^1$, X and n have the meaning stated above therefor, are reacted with hydrogen in the presence of a hydrogenation catalyst.

Examples of hydrocarbon radicals R are alkyl radicals such as the methyl, ethyl, n-propyl, isopropyl, 1-n-butyl, 2-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,2-trimethylpentyl radical, nonyl radicals such as the n-nonyl radical, decyl radicals such as the n-decyl radical, and octadecyl radicals such as the n-octadecyl radical; cycloalkyl radicals such as the cyclopentyl, cyclohexyl, cycloheptyl, and methylcyclohexyl radicals; alkenyl radicals such as the vinyl, allyl, 3-butenyl, 5-hexenyl, 1-propenyl and 1-pentenyl radicals; alkynyl radicals such as the ethynyl, propargyl, and 1-propynyl radicals; aryl radicals such as the phenyl, naphthyl, anthryl and phenanthryl radicals; alkaryl radicals, such as o-, m- and p-tosyl radicals, xylyl radicals, and ethylphenyl radicals; and aralkyl radicals such as the benzyl radical, the phenylethyl radical and the phenylnonyl radical.

Examples of substituted hydrocarbon radicals R are haloalkyl rad//icals such as the 3,3,3-trifluoro-n-propyl radical, the 2,2,2,2',2',2'-hexafluoroisopropyl radical, and the heptafluoroisopropyl radical; haloaryl radicals such as the o-, m- and p-chlorophenyl radicals; and hydrocarbon radicals substituted by amino, mercapto and ammonium groups and having 1 to 18 carbon atoms.

The radical R is preferably a hydrogen atom or a monovalent hydrocarbon radical having 1 to 18 carbon atom(s) per radical, the hydrogen atom, and the methyl and ethyl radicals being particularly preferred.

Examples of unsubstituted and substituted radicals R are all applicable also to radicals $R^1$. The radical $R^1$ is preferably a hydrogen atom or a monovalent hydrocarbon radical having 1 to 18 carbon atom(s) per radical, the hydrogen atom and the methyl and ethyl radicals being particularly preferred.

Examples of X are fluorine, chlorine, bromine and iodine, chlorine being preferred.

Preferred examples for halogenated 1,2-disilaethanes of the formula (I) are:
1,2-bis(chlorodimethylsilyl)ethane,
1,2-bis(dichloromethylsilyl)ethane,
1,2-bis(trichlorosilyl)ethane,
1,2-bis(chlorodiethylsilyl)ethane,
1,2-bis(dichloroethylsilyl)ethane,
1-(chlorodimethylsilyl)-2-(dichloromethylsilyl)ethane,
1,2-bis(chlorodimethylsilyl)propane,
1,2-bis(chlorodimethylsilyl)butane and
2,3-bis(chlorodimethylsilyl)butane.
Particularly preferred 1,2-disilaethanes(I) are:
1,2-bis(chlorodimethylsilyl)ethane,
1,2-bis(dichloromethylsilyl)ethane, and
1,2-bis(trichlorosilyl)ethane.

Further examples of halogenated 1,2-disilaethanes of the formula (I) are the corresponding fluorine, bromine and iodine derivatives of the examples above, the corresponding bromine derivatives being preferred.

Preferred examples of the halogenated 1,2-disilaethenes of the formula (II) which are used in the process according to the invention are the cis and trans isomers of
1,2-bis(chlorodimethylsilyl)ethene,
1,2-bis(dichloromethylsilyl)ethene,
1,2-bis(trichloromethyl)ethene,
1,2-bis(chlorodiethylsilyl)ethene,
1,2-bis(dichloroethylsilyl)ethene,
1-(chlorodimethylsilyl)-2-(dichloromethylsilyl)ethene,
1,2-bis(chlorodimethylsilyl)prop-1-ene,
1,2-bis(chlorodimethylsilyl)but-1-ene, and
2,3-bis(chlorodimethylsilyl)but-2-ene.
Particularly preferred are the cis and trans isomers of
1,2-bis(chlorodimethylsilyl)ethene,
1,2-bis(dichloromethylsilyl)ethene, and
1,2-bis(trichlorosilyl)ethene.

Further examples of halogenated 1,2-disilaethenes of the formula (II) are the corresponding fluorine, bromine and iodine derivatives of the foregoing compounds, the corresponding bromine derivatives being preferred.

Halogenated 1,2-disilaethenes are preferably prepared by a hydrosilylation reaction between vinylsilanes and hydridosilanes and subsequent hydrogen abstraction. Halogenated 1,2-disilaethene are obtained as byproducts of 1,2-disilaethane preparation from vinylsilanes and hydridosilanes. In the process according to the invention, halogenated 1,2-disilaethenes of the formula (II) and hydrogen are reacted with one another preferably in a molar ratio (ratio of double bond in (II) to molecular $H_2$) of from 1:0.6 to $1:10^{10}$, more preferably in a molar ratio of from 1:0.8 to $1:10^9$, and most preferably in a molar ratio of from 1:1 to $1:10^8$.

Preferably used hydrogenation-promoting catalysts are homogeneous catalysts, heterogeneous catalysts and catalysts for catalytic transfer hydrogenation, preferably heterogeneous catalysts and homogeneous catalysts, most preferably, heterogeneous catalysts.

Examples of heterogeneous catalysts, i.e. those which are present on supports, are metals of subgroup VIII of the Periodic Table, such as palladium, platinum, nickel, cobalt and iron; copper; mixtures of the above-mentioned metals; metal oxides of the above-mentioned metals, such as rhenium oxide, mixed metal oxides of the above-mentioned metals, and copper chromite; and metal sulfides of the above-mentioned metals, such as cobalt and nickel sulfide and molybdenum sulfide. The metals, e.g. palladium and platinum, are preferred heterogenous catalysts, and palladium is a particularly preferred catalyst.

The metals are preferably present in finely divided form on the supports. Non-limiting examples of supports are active carbon; carbon; inorganic oxides such as silica, alumina, titanium dioxide, zirconium dioxide and silicates; carbonates such as calcium carbonate and barium carbonate; sulfates such as barium sulfate; and organic supports, such as silica-filled polyethyleneimines. Carbon and active carbon are preferred supports.

Examples of homogeneous catalysts are tricarbonylchromium-solvent complexes, cobalt, ruthenium, rhodium, iridium, platinum and titanium compounds and also Ziegler catalysts, cobalt, ruthenium, rhodium, iridium, platinum and titanium compounds being preferred and ruthenium, rhodium, iridium and platinum compounds being particularly preferred.

Examples of catalysts for transfer hydrogenation are palladium, nickel and platinum, palladium and nickel being preferred and palladium being particularly preferred. The catalysts are preferably used in amounts of from 0.01 to 20% by weight, based on the total weight of the halogenated 1,2-disilaethenes of the formula (II) and hydrogen, more preferably in amounts of from 0.1 to 5% by weight, based on the total weight of the halogenated 1,2-disilaethenes of the formula (II) and hydrogen.

The process according to the invention is preferably carried out at a temperature of from −30° C. to +160° C., preferably from +20° C. to +100° C. Furthermore, the process according to the invention is preferably carried out at a pressure of from 0.5 to 500 bar, preferably from 0.6 to 50 bar, more preferably from 0.7 to 20 bar.

The halogenated 1,2-disilaethanes of the formula (I) which are prepared by the subject invention process can not only be isolated as pure substance; they may also be prepared in situ, i.e. they can be obtained directly after the reaction without a further purification step such as distillation, in a purity of from 85 to 99%, preferably from 95 to 99%.

The halogenated 1,2-disilaethanes of the formula (I) which are prepared by the process according to the invention can be isolated by distillation from the reaction mixture; or, after the addition of a suitable solvent, from the corresponding solution; or can optionally be crystallized from solution.

The process according to the invention can be carried out without a solvent, in a nonpolar aprotic or polar aprotic solvent, or a combination of such solvents, the use of no solvent or of an aprotic solvent being preferred, and the use of no solvent being particularly preferred. In the process according to the invention, there is therefore no need to use a solvent, although pure nonpolar aprotic or polar aprotic solvents or mixtures thereof may be used if desired. The solvents may be coordinating or noncoordinating. Preferably, the solvents or mixtures thereof have a boiling point of from 20° C. to 250° C. at 1013 hPa, in particular of from 30° C. to 230° C. at 1013 hPa.

Examples of suitable aprotic organic solvents are hydrocarbons such as saturated linear hydrocarbons, preferably hexane or heptane; saturated cyclic hydrocarbons, preferably cyclohexane; unsaturated hydrocarbons, preferably aromatic hydrocarbons such as benzene, toluene or xylene; ethers, preferably diethyl ether, di-n-butyl ether, tert-butyl methyl ether, dimethoxyethane or cyclic ethers; or other, heteroatom-substituted compounds, such as, for example, amines, preferably tributylamine or pyridine. Hexane and heptane are particularly preferred.

When solvents are used, they are preferably employed in amounts of 0.01–1000, in particular 1–100, equivalents by weight, based on the total weight of the halogenated 1,2-disilaethenes of the formula (II). The solvents are preferably removed after the reaction. The process has the advantage that halogenated 1,2-disilaethanes of the formula (I) are obtained in high yield and purity in a short reaction time. Furthermore, apart from the catalyst, the process requires no additional activation, for example by a solvent.

In the process according to the invention, the reaction residues which are obtained in the preparation of alkenylsilanes (in particular vinylsilanes) and contain halogenated 1,2-disilaethenes are preferably used as halogenated 1,2-disilaethenes of the formula (II). Reaction residues which are obtained in the preparation of chlorodimethylvinylsilanes and contain 1,2-bis(chlorodimethylsilyl)ethene are preferably used as halogenated 1,2-disilaethenes of the formula (II).

The alkenylsilanes are preferably prepared by an addition reaction between silanes having Si-bonded hydrogen atoms, the other silicon valences being saturated by halogen atoms and/or monovalent hydrocarbon radicals, with an optionally substituted acetylene, in the presence of catalysts promoting the addition of Si-bonded hydrogen at an aliphatic multiple bond, so-called "hydrosilylation catalysts," such as platinum catalysts. The process is described in German Offenlegungsschrift 2 131 741 and the corresponding U.S. Pat. No. 3,798,252 published on Mar. 19, 1974, Wacker-Chemie GmbH, incorporated herein by reference.

Chlorodimethylvinylsilane is preferably prepared by an addition reaction of dimethylchlorosilane with acetylene in the presence of catalysts promoting the addition of Si-bonded hydrogen at an aliphatic multiple bond. The preparation of chlorodimethylvinylsilane is best described in example 12 of the above-mentioned U.S. Pat. No. 3,798,252.

The reaction residue, preferably distillation residue, consists of a mixture of 1,2-bis(chlorodimethylsilyl)ethane, 1,2-bis(chlorodimethylsilyl)ethene and other polychlorinated compounds which cannot be separated by fractional distillation by conventional means. The process according to the invention therefore proves particularly advantageous in the working-up of distillation residues, which would otherwise have to be disposed of in an expensive manner.

1,2-bis(chlorodimethylsilyl)ethane and 1,2-bis(chlorodimethylsilyl)-ethene obtained can be recycled to a very great extent (about 70% by weight) by the process according to the invention. By working up the reaction residue or the products of the secondary reaction, it will no longer be necessary, owing to the large amounts occurring on the world market, to carry out syntheses of, for example, 1,2-bis(chlorodimethylsilyl)ethane which consume raw materials. It is therefore a particularly environmentally friendly and economical process.

The 1,2-disilaethanes of the general formula (I) prepared by the subject invention process are used, in particular, for synthetic purposes, for example in the area of pharmaceutical synthesis, agrochemistry or polymer chemistry, or as solvents, for analytical purposes, and for academic purposes. It is possible, for example, to carry out reactions such as substitution, deprotonation and addition reactions, etc., on 1,2-disilaethanes.

The 1,2-disilaethanes prepared by the process according to the invention, preferably 1,2-bis(chlorodimethylsilyl) ethane, may be used as protective groups for amines in the area of organic pharmaceutical synthesis.

1,2-bis(chlorodimethylsilyl) ethane is the reagent most frequently used for the preparation of stabase adducts. Basic primary amines (pKa about 10–11) form stabase-adducts in high yields at room temperature in the presence of triethylamine in dichloromethane. Various aliphatic amines, α-amino acid esters, methyl 6-aminopenicillanate, N,N-dialkylhydrazines and θ-isiodoanilines may be protected by this method. Less basic amines (generally anilines, pKa about 4–5) require more drastic conditions (n-butyl lithium/diethyl ether/–78° C.).

In the examples described below, all parts and percentages, unless indicated otherwise, are based on weight. Furthermore, all viscosity data are based on a temperature of 25° C. Unless stated otherwise, the examples below were carried out at a pressure of the surrounding atmosphere, i.e. about 1000 hPa, and at room temperature, i.e. at about 20° C., or at a temperature which is established on combining the reactants at room temperature without additional heating or cooling. The hydrogenations were carried out in a 1 liter pressure autoclave.

EXAMPLE 1

Preparation of 1,2-bis(chlorodimethylsilyl)ethane $C_6H_{14}Si_2Cl_2$ $H_2$ gas was forced into 300.0 g (1.41 mol) of 1,2-bis (chlorodimethylsilyl)ethene and 1.5 g(0.7 mmol of pure Pd) of Pd/active carbon while stirring at a temperature of 50° C., until a pressure of 5.0 bar was reached. As a result of the reaction, the pressure gradually decreased again to about 2.0 to 2.5 bar (progressing hydrogenation reaction). Further $H_2$ gas was forced in until a pressure of 5.0 bar was reached. Once again the pressure decreased to 2.0 to 2.5 bar, as a result of the hydrogenation reaction. This process was repeated about 15 to 20 times until the pressure remained constant at 5 bar when further $H_2$ gas was forced in, i.e. no more $H_2$ gas was absorbed by the system. Stirring was then continued for 2 h at a pressure of 5 bar and a temperature of 50° C. After venting, filtration was effected over a pressure drop. The results are summarized in Table 1.

EXAMPLE 2

Preparation of 1,2-bis(dichloromethylsilyl)ethane $C_4H_8Si_2Cl_4$

Example 1 was repeated with the modification that, instead of 300.0 g (1.41 mol) of 1,2-bis(chlorodimethylsilyl) ethene, 300.0 g (1.18 mol) of 1,2-bis(dichloromethylsilyl) ethene were used. The results are summarized in Table 1.

EXAMPLE 3

Preparation of 1,2-bis(trichlorosilyl)ethane $C_2H_2Si_2Cl_6$

Example 1 was repeated with the modification that, instead of 300.0 g (1.41 mol) of 1,2-bis(chlorodimethylsilyl) ethene, 300.0 g (1.02 mol) of 1,2-bis(trichlorosilyl)ethene were used. The results are summarized in Table 1.

EXAMPLE 4

Preparation of 1,2-bis(chlorodiethylsilyl)ethane $C_{10}H_{22}Si_2Cl_2$

Example 1 was repeated with the modification that, instead of 300.0 g (1.41 mol) of 1,2-bis(chlorodimethylsilyl) ethene, 300.0 g (1.11 mol) of 1,2-bis(chlorodiethylsilyl) ethene were used. The results are summarized in Table 1.

EXAMPLE 5

Preparation of 1,2-bis(dichloroethylsilyl)ethane $C_6H_{12}Si_2Cl_4$

Example 1 was repeated with the modification that, instead of 300.0 g (1.41 mol) of 1,2-bis(chlorodimethylsilyl) ethene, 300.0 g (1.06 mol) of 1,2-bis(dichloroethylsilyl) ethene were used. The results are summarized in Table 1.

EXAMPLE 6

Preparation of 1-(chlorodimethylsilyl)-2-(dichloromethylsilyl)ethane $C_5H_{11}Si_2Cl_3$ Example 1 was repeated with the modification that, instead of 300.0 g (1.41 mol) of 1,2-bis(chlorodimethylsilyl) ethene, 300.0 g (1.28 mol) of 1-(chlorodimethylsilyl)-2-(dichloromethylsilyl)ethene were used. The results are summarized in Table 1.

EXAMPLE 7

Preparation of 1,2-bis(chlorodimethylsilyl)propane
$C_7H_{16}Si_2Cl_2$

Example 1 was repeated with the modification that, instead of 300.0 (1.41 mol) of 1,2-bis(chlorodimethylsilyl)ethene, 300.0 g (1.32 mol) of 1,2-bis(dichlorodimethylsilyl)prop-1-ene were used. The results are summarized in Table 1.

EXAMPLE 8

Preparation of 1,2-bis(chlorodimethylsilyl)-butane
$C_8H_{18}Si_2Cl_2$

Example 1 was repeated with the modification that, instead of 300.0 g (1.41 mol) of 1,2-bis(chlorodimethylsilyl)ethene, 300.0 g (1.24 mol) of 1,2-bis(dichloromethylsilyl)but-1-ene were used. The results are summarized in Table 1.

EXAMPLE 9

Preparation of 2,3-bis (chlorodimethylsilyl)butane
$C_9H_{18}Si_2Cl_2$

Example 1 was repeated with the modification that, instead of 300.0 g (1.41 mol) of 1,2-bis(chlorodimethylsilyl)ethene, 300.0 g (1.24 mol) of 2,3-bis(dichloromethylsilyl)but-2-ene were used. The results are summarized in Table 1.

EXAMPLE 10

Working-up of Distillation Residues of the Chlorodimethylvinylsilane ($VM_2$) Preparation I Chlorodimethylvinylsilane is prepared by a hydrosilylation reaction of chlorodimethylsilane and acetylene. Distillation residues contain considerable amounts of 1,2-bis(chlorodimethylsilyl)ethane and 1,2-bis(chlorodimethylsilyl)ethene in addition to other residues.

$H_2$ gas was forced into a mixture of 300.0 g (294 ml) of $VM_2$ residue comprising 1,2-bis(chlorodimethylsilyl)ethane, 1,2-bis(chlorodimethylsilyl)ethene and other compounds, including polychlorinated compounds, and 1.5 g (0.7 mmol of pure Pd) of Pd/active carbon while stirring at a temperature of 50° C., until a pressure of 5.0 bar was reached. As a result of the reaction, the pressure gradually dropped again to about 2.0 to 2.5 bar (progressing hydrogenation reaction). Further $H_2$ gas was forced in until a pressure of 5.0 bar was reached. The pressure dropped again to 2.0 to 2.5 bar as a result of the hydrogenation reaction. This process was repeated about 15 to 20 times until the pressure remained constant at 5 bar on forcing in further $H_2$, gas, i.e. no more $H_2$ gas was absorbed by the system. Stirring was then continued for 2 h at a pressure of 5 bar and a temperature of 50° C.

After the apparatus had been vented, filtration was effected via a pressure filter, and distillation effected over a 30 cm packed column at a pressure of 5 bar and a temperature of 75–80° C. The results are summarized in Table 1.

EXAMPLE 11

Working-up of Distillation Residues of the Chlorodimethylvinylsilane ($VM_2$) Preparation I Chlorodimethylvinylsilane is prepared by a hydrosilylation reaction of chlorodimethylsilane and acetylene. Distillation residues contain considerable amounts of 1,2-bis(chlorodimethylsilyl)ethane and 1,2-bis(chlorodimethylsilyl)ethene in addition to other residues.

445.1 g (437 ml) were subjected to a fractional distillation. $H_2$ gas was forced into 261.0 g (256 ml) of $VM_2$ residue from the fractionation, (comprising 1,2-bis(chlorodimethylsilyl)ethane, 1,2-bis(chlorodimethylsilyl)ethene) and 1.5 g (0.7 mmol of pure Pd) of Pd/active carbon while stirring at a temperature of 50° C., until a pressure of 5.0 bar was reached. As a result of the reaction, the pressure gradually dropped again to about 2.0 to 2.5 bar. Further $H_2$ gas was forced in until a pressure of 5.0 bar was reached. The pressure dropped again to 2.0 to 2.5 bar as a result of the hydrogenation reaction. This process was repeated about 15 to 20 times until the pressure remained constant at 5 bar on forcing in further $H_2$ gas, i.e. no more $H_2$ gas was absorbed by the system. Stirring was then continued for 2 h at a pressure of 5 bar and a temperature of 50° C.

After the apparatus had been vented, filtration was effected via a pressure filter. The results are summarized in Table 1.

EXAMPLE 12

Working-up of Distillation Residues of the Chlorodimethylvinylsilane ($VM_2$) Preparation I Chlorodimethylvinylsilane is prepared by a hydrosilylation reaction of chlorodimethylsilane and acetylene. Distillation residues contain considerable amounts of 1,2-bis(chlorodimethylsilyl)ethane and 1,2-bis(chlorodimethylsilyl)ethene in addition to other residues.

445.1 g (437 ml) were subjected to a fractional distillation. $H_2$ gas was forced into 261.0 g (256 ml) of $VM_2$ residue (comprising 1,2-bis(chlorodimethylsilyl)ethane, 1,2-bis(chlorodimethylsilyl)ethene) and 1.5 g (0.7 mmol of pure Pd) of Pd/active carbon while stirring at a temperature of 50° C., until a pressure of 5.0 bar was reached. As a result of the reaction, the pressure gradually dropped again to about 2.0 to 2.5 bar. Further $H_2$ gas was forced in until a pressure of 5.0 bar was reached, where the pressure dropped again to 2.0 to 2.5 bar. This process was repeated about 15 to 20 times until the pressure remained constant at 5 bar on forcing in further $H_2$ gas, i.e. no more $H_2$ gas was absorbed by the system. Stirring was then continued for 2 h at a pressure of 5 bar and a temperature of 50° C.

After the apparatus had been vented, filtration was effected via a pressure filter and distillation effected over a 30 cm packed column at a pressure of 5 bar and a temperature of 75–80° C. The results are summarized in Table 1.

EXAMPLE 13

Preparation of 1,2-bis(chlorodimethylsilyl)ethane by homogeneous catalysis

Example 1 was repeated with the modification that, instead of 1.5 g (0.7 mmol of pure Pd) of palladium/active carbon, 0.7 g (0.7 mmol) of (triphenylphosphine)ruthenium (II) dichloride were used. The results are summarized in Table 1.

EXAMPLE 14

Preparation of 1,2-bis(chlorodimethylsilyl)ethane by catalytic transfer hydrogenation Example 1 was repeated with the modification that, instead of 1.5 g (0.7 mmol of pure Pd) of Pd/active carbon and $H_2$ gas, 1.5 g (0.7 mmol of pure Pd) and 127.4 g (1.55 mol) of cyclohexene were used. The results are summarized in Table 1.

TABLE 1

Yields [G], Yields [%] and Purities Obtained in Examples 1 to 14

| Example | Yield [g] | Yield [%] | Purity [%] |
|---|---|---|---|
| 1 | 299.9 | 99 | 99 |
| 2 | 296.3 | 98 | 99 |
| 3 | 292.8 | 97 | 99 |
| 4 | 290.1 | 96 | 98 |
| 5 | 289.8 | 96 | 98 |
| 6 | 290.6 | 96 | 98 |
| 6 | 290.6 | 96 | 98 |
| 7 | 293.6 | 97 | 98 |
| 8 | 293.4 | 97 | 98 |
| 9 | 293.4 | 97 | 98 |
| 10 | 177.9 | 88* | 99 |
| 11 | 261.0 | 87* | 99 |
| 12 | 231.0 | 77* | 99 |
| 13 | 293.8 | 97 | 98 |
| 14 | 293.8 | 97 | 98 |

*Based on 1,2-bis(chlorodimethylsilyl)ethane and 1,2-bis(chlorodimethylsilyl)ethene fraction in the mixture.

What is claimed is:

1. A process for the preparation of halogenated 1,2-disilaethanes of the general formula $$X_{3-n}R_nSi\text{---}CHR^1CHR^1\text{---}SiR_nX_{3-n} \quad (I)$$

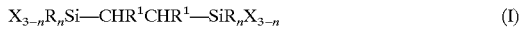

in which R are identical or different and are a hydrogen atom or a monovalent, optionally substituted hydrocarbon radical having 1 to 40 carbon atom(s) per radical, $R^1$ are identical or different and are a hydrogen atom or a monovalent optionally substituted hydrocarbon radical having 1 to 40 carbon atom(s) per radical, X are a halogen atom, and n denotes 0, 1 or 2, wherein halogenated 1,2-disilaethenes of the general formula $$X_{3-n}R_nSi\text{---}CR^1\text{=}CR^1\text{---}SiR_nX_{3-n} \quad (II)$$

in which R, $R^1$, X and n have the meaning stated above therefor, are reacted with hydrogen in the presence of a hydrogenation catalyst.

2. The process of claim 1, wherein R is a methyl radical.
3. The process of claim 1, wherein $R^1$ is a hydrogen atom.
4. The process of claim 2, wherein $R^1$ is a hydrogen atom.
5. The process of claim 1, wherein X is a chlorine atom.
6. The process of claim 2, wherein X is a chlorine atom.
7. The process of claim 3, wherein X is a chlorine atom.
8. The process of claim 1, wherein said halogenated 1,2-disilaethene is 1,2-bis(chlorodimethylsilyl)ethene.
9. The process of claim 2, wherein said halogenated 1,2-disilaethene is 1,2-bis(chlorodimethylsilyl)ethene.
10. The process of claim 3, wherein said halogenated 1,2-disilaethene is 1,2-bis(chlorodimethylsilyl)ethene.
11. The process of claim 5, wherein said halogenated 1,2-disilaethene is 1,2-bis(chlorodimethylsilyl)ethene.
12. The process of claim 1, wherein the reaction residues obtained from the preparation of alkenylsilanes and containing halogenated 1,2-disilaethenes, are used as said halogenated 1,2-disilaethenes.
13. The process of claim 12, wherein the alkenylsilanes are prepared by an addition reaction between
   a) silanes having Si-bonded hydrogen atoms, the other silicon valences being saturated by halogen atoms and/or monovalent hydrocarbon radicals,
   b) optionally substituted acetylene,
   c) in the presence of catalysts promoting the addition of Si-bonded hydrogen at an aliphatic multiple bond.
14. The process of claim 12, wherein the reaction residues obtained in the preparation of chlorodimethylvinylsilane, containing 1,2-bis(chlorodimethylsilyl)ethene, are used as halogenated 1,2-disilaethenes.
15. The process of claim 14, wherein chlorodimethylvinylsilane is prepared by an addition reaction of chlorodimethylsilane with acetylene in the presence of catalysts promoting the addition of Si-bonded hydrogen at an aliphatic multiple bond.

* * * * *